United States Patent [19]

Terasawa et al.

[11] Patent Number: 5,279,951
[45] Date of Patent: Jan. 18, 1994

[54] CULTIVATION OF TRANSFORMED MICROORGANISMS

[75] Inventors: Masato Terasawa, Ami; Hisashi Yamagata, Toride; Hideaki Yukawa, Ami; Yasurou Kurusu, Ami; Makiko Fukushima, Ami, all of Japan

[73] Assignee: Research Association for Utilization of Light Oil, Tokyo, Japan

[21] Appl. No.: 519,776

[22] Filed: May 7, 1990

[30] Foreign Application Priority Data

May 8, 1989 [JP] Japan .................................. 1-113847
Feb. 28, 1990 [JP] Japan .................................. 2-45724
Mar. 1, 1990 [JP] Japan .................................. 2-47192

[51] Int. Cl.$^5$ ..................... C12N 1/21; C12N 15/11; C12N 15/70; C12N 15/71
[52] U.S. Cl. ..................... 435/172.3; 435/252.33; 435/320.1; 435/849; 536/23.2; 536/23.7; 536/24.1; 935/29; 935/40; 935/41; 935/43
[58] Field of Search ............ 435/69.1, 108, 172.3, 435/252.33, 320.1, 69.8; 935/29, 40, 41, 43; 536/27, 24.1, 23.2

[56] References Cited

FOREIGN PATENT DOCUMENTS 0180192 5/1986 European Pat. Off. .
0279664 8/1988 European Pat. Off. .
0281104 9/1988 European Pat. Off. .
60-02189 1/1985 Japan .
61-239896 10/1986 Japan .
63-28393 2/1988 Japan .

OTHER PUBLICATIONS

Botsford, J. L. et al. *J. Bacteriol.* 105:303-312 (1971).
Zaffaroni et al., *Agr. Biol. Chem.*, 38(7) pp. 1335-1342 (1974).
Nichols, B. P. et al. *Methods in Enzymology* 101:155-164 (1983).

*Primary Examiner*—Robert A. Wax
*Assistant Examiner*—Dian Jacobson
*Attorney, Agent, or Firm*—Wenderoth, Lind & Ponack

[57] ABSTRACT

A process for cultivating a microorganism transformed with a recombinant plasmid at least containing (a) a DNA fragment containing a promoter and a regulator gene tnaC located downstream of the promoter in a tryptophanase operon (tna), and (b) a DNA fragment containing a desired structural gene which can be expressed by the promoter, which comprises cultivating the transformed microorganism in a culture medium while adding glucose as a carbon source continuously or intermittently so that the concentration of glucose is maintained within the range of 0.01 to 0.3%, and thereby allowing the desired structural gene to be expressed in the microorganism.

10 Claims, 2 Drawing Sheets

CULTIVATION OF TRANSFORMED MICROORGANISMS

BACKGROUND OF THE INVENTION

This invention relates to a process for cultivating a microorganism which comprises cultivating a microorganism transformed with a recombinant plasmid containing the desired structural gene derived from an animal, plant or microorganism which can be expressed by a promoter in a tryptophanase operon, and thereby producing large amounts of the desired gene product, to novel recombinant plasmids which can be used in the process, and to microorganism transformed with the plasmids.

There have recently been striking advances in the DNA recombinant technology of producing large amounts of useful substances by using host microorganisms containing recombinant plasmids which include homologous or heterologous DNA fragments bearing encoding the genetic information of useful substances derived from animals, plants or microorganisms. Production of insulin or interferon using Escherichia coli as a host microorganism has already been under way.

In spite of the advances in the DNA recombinant technology, however, no process for producing large amounts of the desired useful substance using recombinant plasmids containing the desired structural gene has yet been established, and the development of a process for cultivating transformants efficiently is urgently in need.

On the other hand, the regulation of expression of a tryptophanase operon (TNa) is controlled by a mechanism, called "catabolite repression" (J. L. Botsford and R. D. DeMoss; J. Bacteriol, 1971, 105, 303-312). It is known that in a culture medium containing glucose as a main carbon source, the expression of the tryptophanase structural gene is very strongly incubated.

Although the promoter in the tryptophanase operon has a high potential to express the desired structural gene, it is necessary to use an expensive carbon source for cultivation such as succinic acid instead of glucose. It is a great problem to develop an efficient gene expression system potentiated by the tna promoter that uses glucose, which is cheap and industrially valuable, but up to the present invention it could not be used as a carbon source for cultivation.

The present inventors extensively studied the effective utilization of the promoter in the tryptophanase operon (tna), and consequently found that by placing a DNA fragment (b) containing the structural gene downstream of a DNA fragment (a) containing both a tna promoter and a regulatory gene tnaC in this order, not only the tryptophanase structural gene but also a foreign structural gene can be expressed strongly by the above promoter.

The regulatory gene tnaC is a short coding region which is located between the tryptophanase promoter and tryptophanase structural gene tnaA and is responsible for the regulation of expression of the tryptophanase operon through a mode, called "transcriptional antitermination" [V. Stewart and C. Yanofsky; J. Bacteriol., 164 (1985) 731-740].

In spite of the fact that a microorganism transformed with a recombinant plasmid containing at least the DNA fragments (a) and (b) undergoes the above-mentioned catabolite repression (the inhibition of gene expression by glucose), if glucose is added continuously or intermittently so that its concentration is maintained at a specified low value in a culture medium containing L- or DL-tryptophan, the present inventors surprisingly found that the transformed microorganism does not undergo catabolite repression, and the desired gene was expressed highly, and the expression product can be obtained in large amounts.

As a method of cultivating a microorganism while glucose is added to the culture medium continuously or intermittently in some low concentrations, Japanese Patent Publication No. 42555/1986 already disclosed a method of cultivating a tryptophan synthase-producing Escherichia coli strain by adding glucose continuously or intermittently so that its concentration in the culture medium is maintained at 1% or less.

It is known that the expression of a tryptophan synthase gene is controlled by a promoter in a tryptophan operon, and this gene expression mechanism does not undergo catabolite repression.

In fact, Agr. Biol. Chem., 38 (7), 1335-1334, 1974 states that when tryptophan synthase-producing Escherichia coli, was cultivated in a medium containing glucose at 0.5 and 1.8% concentration, the tryptophan synthase activity of the cells was 2.4 and 7.3 U/ml respectively, showing that the enzyme activity increases as the concentration of glucose increases. Japanese Patent Application Publication No. 268175/1986 discloses that when cultivating the tryptophan synthase-producing Escherichia coli with a concentration of glucose in the culture medium maintained at 0.5 to 5%, the tryptophan synthase activity shows the highest value.

The above-cited Japanese Patent Publication No. 42555/1986 discloses in the example, that, compared to the values attained at the glucose concentration in the medium initially set at 5.0%, cells yield increased to 2.69 times and the enzyme activity increased 1.80 times (glucose concentration of 1%), cell yield and enzyme activity increased 3.1 times and 2.15 times for a (glucose concentration maintained 0.05%). From the results, at lower concentrations of glucose, both the cells yield and the enzyme activity tended to show an increase. But the difference is only slight. There is no disclosure that tryptophan synthase gene is expressed by the promoter of the tryptophanase operon (tna). Furthermore, when the gene expression is inhibited by catabolite repression, only the expression of the gene is inhibited irrespective of the cell growth. As stated above, the Escherichia coli used in Japanese Patent Publication No. 42555/1986 is controlled by glucose both in the amount of the cells recovered and the enzyme activity.

It is considered that the phenomenon disclosed in Patent Publication No. 42555/1986 is entirely different from "catabolite repression" and is quite unique and specific only for Escherichia coli strains cited in the above patent document.

As far as the present inventors know, there has been no disclosure on the cultivation methods of recombinant Escherichia coli strains utilizing the tna mediated gene promoter expression system.

SUMMARY OF THE INVENTION

According to this invention, there is provided a process for cultivating a microorganism transformed with a recombinant plasmid at least containing (a) a DNA fragment containing a promoter in a tryptophanase operon (tna), and a regulatory gene tnaC located downstream of the promoter and (b) a DNA fragment containing a desired structural gene downstream of (a) which can be express by the promoter, which comprises cultivating the transformed microorganism in a culture medium containing L- or DL-tryptophan as inducer of the structural gene and glucose as a carbon source, the concentration of glucose being maintained in the range of 0.01 to 0.3% (wt/vol) by continuous or intermittent addition to the medium, thereby allowing the desired structural gene to be expressed in the microorganism.

DETAILED DESCRIPTION OF THE PREFERRED EMBODIMENTS

The cultivation process in accordance with this invention will be described below in greater details.

I. Transformed microorganism

The microorganism to be cultivated by the process of this invention is a microorganism to be transformed with a recombinant plasmid containing
(a) a DNA fragment containing a promoter in a tryptophanase operon (tna) and a regulatory gene tnaC located downstream of the promoter (to be sometimes abbreviated as "P fragment") and
(b) a DNA fragment containing a desired structural gene which can be expressed by the promoter (to be sometimes abbreviated as "T fragment").

The transformed microorganism will be described below.

I-1. Recombinant plasmid

The recombinant plasmid to be introduced into the host microorganism at least contains the DNA fragment (a) (P fragment) and the DNA fragment (b) (T fragments). And it can be stably maintained in the host microorganism and replicate.

The P fragment, bearing the function of expressing the desired structural gene under its control, is preferably originated from a chromosomal DNA of *Escherichia coli*. Advantageously used as chromosomal DNAs of *E. coli* ATCC 27325, *E. coli* ATCC 23282, *E. coli* ATCC 23437 and *E. coli* ATCC 23461.

The method for isolating the P fragment from these microorganisms is described in Example 1, (1) and Example 2, (2). Its basic procedure will be described briefly. A chromosomal DNA containing a tryptophanase operon is extracted from *Escherichia coli* cells as described by Saito and Miura [H. Saito and K. Jiura: Biochem. Biophys. Acta 72, 619–629 (1963)]. The chromosomal DNA is digested with suitable restriction endonucleases, and a DNA fragment containing a promoter in the tryptophanase operon (tna) and a regulatory gene tnaC. For example, if it is digested with restriction endonucleases BamHI and HindIII, a tryptophanase operon (tna DNA fragment having a molecular size of about 3.2 kb can be obtained. If this DNA fragment is further digested with restriction endonucleases AluI and RsaI, a DNA fragment (about 630 bp) containing the tna promoter and the regulatory gene tnaC can be obtained. This DNA fragment can be used as the P fragment.

If the desired structural gene in the T fragment is a tryptophanase structural gene (tnaA), the above tryptophanase operon (tna) DNA fragment having a molecular size of about 3.2 kb or an about 2.3 kb DNA fragment prepared by deleting about 900 bp from the BamHI site of the above DNA fragment with exonuclease III may be used as a DNA fragment containing both the P and T fragments.

On the other hand, the "desired structural gene" contained in the T fragment includes those encoding genetic information corresponding to proteins or peptides of interest derived from any origin which can be expressed by the P fragment.

Typical examples of such structural genes include tryptophanase E. C. 4. 1. 99. 1), tryptophan synthase (E.C.4.2.1.20), chloramphenicol acetyltransferase (E.C.2.3.1.28), aspartase (E.C.4.3.1.1), threonine synthase (E.C.4.2.99.2S), homoserine kinase (E.C.2.7.1.39), various growth hormones, insulin, somatostatin, interferon and interleukin. DNA fragments (T fragment) containing the desired structural genes bearing the genetic information of these useful substances can be obtained from the cells of animals, plants or microorganisms by known methods. In the present invention, those derived from *Escherichia coli* are suitably used.

For example, a DNA fragment containing tryptophanase structural gene (tnaA) or tryptophan syn those structural genes (trpA, trpB) are preferable, and its desirable origins are *Escherichia coli* K-12 strain, particularly *E. coli* ATCC 27325, *E. coli* ATCC 23282, *E. coli* ATCC 2347 and *E. coli* ATCC 23461.

Examples of a DNA fragment containing the tryptophanase structural gene (tnaA) are a tryptophanase operon (tna) DNA fragment having a molecular size of about 3.2 kb obtained by digesting the above *E. coli* chromosomal DNA with restriction endonucleases BamHI and Hind III, and an about 2.3 kb DNA fragment obtained by deleting about 900 bp from the BamHI site of the above DNA. These DNA fragments contain both the structural gene of tryptophanase (tnaA) and promoter and regulatory gene in a desired order so that they can be directly used in the present invention.

An example of the DNA fragment containing tryptophan synthase structural genes (trpA, trpB) is a DNA fragment having a molecular size of about 2.6 kb and containing tryptophan synthase structural genes (trpA, (trpB). It can be obtained by infecting the above *E. coli* with phage φ (phi) 80, inducing it to lytic cycle to prepare a large amount of phage particle, then extracting the phage DNA, digesting it with restriction endonuclease BamHI to obtain a DNA fragment with a length of about 20 kb containing the tryptophan operon, and partially digesting it with restriction endonuclease HincII to give the above 2.6 kb fragment.

Examples of other DNA fragments which the recombinant plasmid in accordance with this invention can contain include a DNA fragment containing a gene governing the autonomous replication of Col El-type plasmids, a DNA fragments containing a gene encoding the plasmid partition system derived from F plasmid, and a DNA fragment containing genes encoding the resistances of antibiotics (such as ampicillin, kanamycin and chloramphenicol).

One specific example of a preferred recombinant plasmid used in this invention is a plasmid comprising (a) a DNA fragment (P fragment) containing a tryptophanase promoter and a regulatory gene (tnaC) located downstream of the promoter, (b) a DNA fragment (T fragment) containing the desired structural gene that can be expressed by the promoter, (c) a DNA fragment containing genes governing the autonomous replication of a Col El-type plasmid, and (d) a DNA fragment containing a gene encoding the plasmid partition system derived from an F-plasmid.

The DNA fragment (c) used in combination with the P fragment and the T fragment, that is, "the DNA fragment containing a gene governing the autonomous replication derived from a Col El type plasmid" (to be abbreviated as "S fragment", includes a DNA fragment containing a region responsible for the autonomous replication of a Col El-type plasmid, the copy number of which is 20 to 30 per chromosome. Typical examples of this S fragment are an S fragment having a molecular size of about 4.3 kb derived from plasmid pBR322, an S fragment having a molecular size of about 5.1 kb derived from plasmid pkk232, and an S fragment derived from plasmid pBR325.

Figure 1:
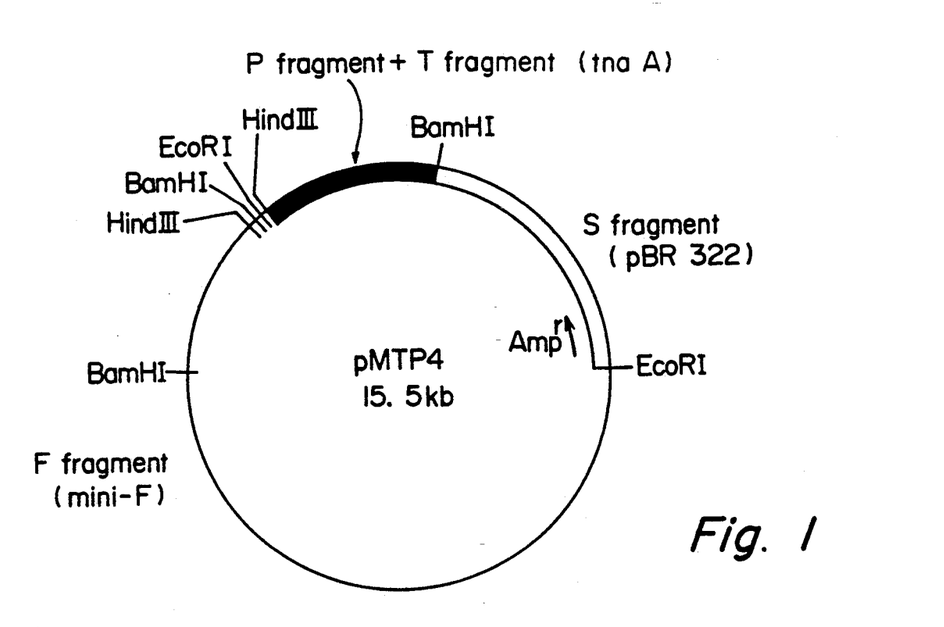
FIG. 1 shows plasmid pMTP4 which comprises
(a) a DNA fragment (P+T fragment containing a tryptophanase promoter and regulatory gene tnaC located downstream of the promoter and a tryptophanase structural gene (tnaA),
(b) a DNA fragment (S fragment) containing the replication origin of plasmid pBR322, and
(c) a mini-F fragment (F fragment) obtained from F-plasmid.

The P fragment, the T fragment and the S fragment are further combined with the DNA fragment (d) containing a gene encoding the plasmid partition system derived from an F plasmid. The F plasmid is a known plasmid having a molecular size of 94.5 kb ($62 \times 10^6$ daltons) having a structure described, for example, in the genetic map and physical map of a plasmid made by ECoRI as shown in FIG. 1 at page 98 of "Protein, Nucleic acid and Enzymes", vol. 27, No. 1 (1982). It exists in enteric bacteria such as *Escherichia coli* with a copy number of 1-2 per chromosome. This plasmid has such a mechanism that after the cell division. This has a mechanism that it is stably partitioned to daughter cells upon the division of host, thus free segregation (such a mechanism that synchronizes the replication of the plasmid to its host cell cycle is called "stringent control"). It has already been found that such a function of stringently controlling proliferation in the F-plasmid is carried out on a fragment, called mini-F, which has a molecular size of 9.2 kb and can replicate autonomously [see "Molecular & General Genetics", 196, 185-193 (1984)]. It is also known that the mini-F can be cut out from the P fragment with restriction endonuclease EcoRI.

The plasmid in accordance with this invention utilizes the plasmid partition system encoded by the mini-F. Thus, the "DNA fragment containing genes which encodes the plasmid partition system and derived from the F-plasmid is abbreviated as the "F fragment". The F fragment functions to prevent the appearance of plasmid-free segragrant by stable inheritance to daughter cells. A typical example is a mini-F fragment having a molecular size of about 9.2 kb which can be cut out using restriction endonuclease EcoRI. The plasmid that can be used in this invention may contain another DNA fragment bearing another genetic information, such as a DNA fragment containing an ampicillin-resistance gene or a kanamycin-resistance gene as an antibiotic resistance marker so long as it essentially contains the above described P fragment, T fragment, S fragment and F fragment.

Construction of the recombinant plasmid from these DNA fragments may be carried out by known methods as described in a standard textbook on gene manipulation, [T. Maniatis, E. F. Fritsch and J. Sambrook, "Molecular Cloning", Cold Spring Harbor Laboratory (1982)].

A typical example of the recombinant plasmid that can be used in this invention consists substantially of four DNA fragments, i.e., the P fragments, T fragment, S fragments and T fragment. More specific examples include (1) a plasmid having a molecular size of about 10.2 megadaltons about 15.5 kb) in which the T fragment contains tryptophanase structural gene (tnaA). This plasmid is named "plasmid pMTP4" by the present inventor (see Example 1);

(2) plasmids pMTP1 and pMTP1R having a molecular size of about 10.7 megadaltons (about 15.4 kb) (these plasmids and their method of preparation are disclosed in Japanese Laid-Open Patent Publications No. 28393/1988, and the description of this patent document is cited herein in lieu of describing them in detail);

(3) A plasmid having a molecular size of about 9.9 megadaltons (about 16.6 kb) in which the T fragment contains tryptophan synthase structural gene (trpB, trpA). The present inventors names it "plasmid pMTY20" (see Example 2 given hereinafter). Of these, plasmid pdMTP4 and plasmid pMTY20 are preferred. The plasmids pMTP4 and pMTY20 are novel plasmids not described in the prior literature, and constitute part of the present invention.

The plasmid pMTP4 has the following recognition sites of restriction endonucleases and the length of fragments.

| Restriction endonuclease | Plasmid pMTP4 | |
|---|---|---|
| | Number of recognition sites | Length of fragments (kb) |
| EcoRI | 2 | 9.2, 6.3 |
| BamHI | 3 | 2.4, 10.7, 2.4 |
| HindIII | 2 | 14.7, 0.8 |

The pMTP4 having the above characteristics can be constructed, for example, by the following procedure.

First, the DNA fragment (P+T) in which the tryptophanase promoter, the regulatory gene tnaC positioned downstream of the promoter and the tryptophanase structural gene tnaA are joined is prepared, for example, by extracting a chromosomal DNA from, for example, *E. coli* having a tryptophanase operon in its chromosome, for example an *Escherichia coli* K-12 strain (ATCC 23282, ATCC 23437, ATCC 27325 or ATCC 23461) and cutting out a DNA fragment containing tryptophanase operon using restriction endonucleases BamHI and HindIII by a conventional method [T. Maniatis, E. F. Fritsch and J. Sambrook, "Molecular Cloning" (1982), p. 164–165, Cold Spring Harbor Laboratory] to obtain a DNA fragment having a molecular size of about 3.2 kb, and the 900 bp is deleted from the BamHI site of the fragment to obtain (P+T) fragment having a size of about 2.3 kb and containing the tryptophanase promoter, the regulatory gene tnaC located downstream of the promoter, and the tryptophanase structural gene (tnaA).

On the other hand, the mini-F fragment (about 9.2 kb) can be prepared by digesting F plasmid extracted from such strain as E. coli K-12 (ATCC 15153, ATCC 23589 or ATCC 23590), by the method of Guerry et al. [P. Guerry, D. L. La Blanc, S. Falkow: J. Bact., 116, 1064 (1973)] with restriction endonuclease EcoRI.

On the other hand, it is convenient to use plasmid pBR322 as a typical example of Col El plasmid as a source of the DNA fragment containing a gene governing the autonomous replication of Col El plasmid.

The prepared (P+T) fragment is combined with plasmid pBR322 digested with restriction endonucleases BamHI and HindIII and T4 DNA ligase was caused to act on them to prepare a plasmid resulting from incorporating the (P+T) fragment in the plasmid pBR322. Then, the resulting plasmid was cleaved with restriction endonuclease EcoRI and is combined with the mini-F fragment prepared as above. The action of T4 DNA ligase on them gives the desired plasmid pMTP4.

The specific method of preparing the plasmid pMTP4 will be described in detail in Example 1 below.

On the other hand, the plasmid pMTY20 shows the following restriction endonuclease recognition sites and the lengths (kb) of the fragments with the following endonucleases.

| | Plasmid pMTY20 | |
|---|---|---|
| Restriction endonuclease | Number of recognition sites | Length of the fragments (kb) |
| EcoRI | 2 | 9.2, 7.4 |
| HindIII | 3 | 9.3, 5.0, 2.3 |
| SalI | 4 | 12.8, 2.4, 0.8, 0.6 |
| BamHI | 5 | 6.8, 4.0, 2.7, 2.4, 0.7 |

The plasmid pMTY20 having the above characteristics can be produced, for example, by the following procedure.

The DNA fragment containing the tryptophanase promoter and the regulatory gene tnaC located downstream of the promoter may be prepared by extracting a chromosomal DNA from E. coli having a tryptophanase operon, such as an E. coli K-12 strain (ATCC 23282, ATCC 23437, ATCC 27325, or ATCC 23461), and digesting the chromosomal DNA with restriction endonuclease BamHI and HindIII to obtain tryptophanase operon in a customary manner [T. Maniatis, E. F. Fritsch, and J. Sambrook, "Molecular Cloning" (1982), pp. 164–165, Cold Spring Harbor Laboratory]. Further by using restriction endonucleases R SalI and AluI, an about 630 bp DNA fragment containing the tryptophanase promoter and the regulatory gene tnaC located downstream of the promoter can be prepared. Furthermore, a P fragment is obtaining by attaching to both ends a BamHI linker.

The T fragment (a DNA fragment containing a tryprophan synthase structural gene) may be prepared by infecting an E. coli K-12 strain (ATCC 27325, ATCC 23282, ATCC 23437, ATCC 23437 or ATCC 23461 with a phage, such as phage (phi) 80 (ATCC 11456a-B1) and by lysogenization and then by induction a large amount of phage particle with tryprophan operon inside was prepared [R. M. Denney and C. Yanofsky; J. Bacteriol., 118, 505 (1974). The phage DNA is extracted by a customary method [T. Maniatis, E. F. Fritsch and J. Sambrook: "Molecular Cloning" (1982), pp. 164–165, Cold Spring Harbor Laboratory], by using restriction endonucleases such as BamHI, EcoRI, a tryptophan operon DNA fragment is cut out. This DNA fragment is further partially digested with restriction endonuclease HincII to give a DNA fragment containing trpA and trpB genes.

Then, the resulting DNA fragment and a SalI linker are mixed, and ligated by a T4 DNA ligase to give a T fragment having a SalI site at both ends of the trpA/trpB fragment.

The mini-F fragment having a molecular size of about 9.2 kb (F fragment) is prepared by digesting with restriction endonuclease EcoRI the F-plasmid extracted from such as E. coli K-12 (ATCC 15153, ATCC 2389 or ATCC 23590), as described by in P. Guerry, DL. Le Blanc and S. Falkow; J. Bact., 116, 1604.

It is convenient to use plasmid pBR322 typical of a Col El plasmid as a source of the DNA fragment (S fragment) containing a gene governing the autonomous replication of the Col El plasmid.

The P and the T fragment obtained as above is inserted to the BamHI and SalI site, respectively, of a plasmid PUC 119 and digested partially with EcoRI and HindIII to give a fragment containing a tryptophan promoter, a regulatory gene tnaC, and a tryptophan synthase structural gene (trpa, trpB). The resulting DNA fragment is ligated to EcoRI and HindIII digest of plasmid pBR322 (the S fragment) and the H fragment is inserted to the EcoRI site of the resulting plasmid to give desired plasmid pMTY20.

A procedure of preparing the plasmid pMTY20 will be shown in detail in Example 2 below.

I-2. Host Microorganism

Host microorganisms that can be transformed with the recombinant plasmids described in section I-1 are suitably microorganisms belonging to *Escherichia coli*. Depending upon the type of the plasmid, such microorganisms as *Pseudomonas putida, Brevibacterium flavum* and *Bacillus subtilis* may also be used as hosts.

Examples of the microorganisms belonging to *Escherichia coli* are *E. coli* K-12 strains, ATCC 27325, ATCC 23282, ATCC 23437 and ATCC 23461.

I-3. Transformation

The recombinant plasmids described in I-1 are transformed to the host microorganism as described above by methods known per se, for example, M. Mandel and A. Higa: SJ. Mol. Biol., 53, 159 (1970).

Specific examples of microorganisms transformed as above are shown below.

(1) *Escherichia coli* YK3007 (FERM BP-2803) containing the plasmid pMTP4

(2) *Escherichia coli* K-12 YK3002 (FERM BP-1733) containing the plasmid pMTP1, and *Escherichia coli* K-12 YK3003 containing the plasmid pMTP1R (FERM BP-1734)

(3) *Escherichia coli* YK2017 (FERM BP-2804) containing the plasmid pMTY20

The transformed *Escherichia coli* strain are deposited under the above parenthesized FERM numbers at the Fermentation Research Institute, Agency of Industrial Science and Technology, 1-3, Higashi 1-chome, Tsukuba-shi Ibaraki-ken 305, Japan under the Budapest Treaty on the International Recognition of the Deposit of Microorganisms for the purposes of Patent Procedure.

II. Cultivation

The transformed microorganism is cultivated in accordance with the process of this invention in a culture medium containing L- or DL-tryptophan while continuously or intermittently adding glucose as a carbon source to the culture medium so that the concentration of glucose is maintained at 0.01 to 0.3% (wt/vol). As a result, the transformed microorganism does not undergo catabolite repression, but the gene expression mechanism of the promoter in the tryptophanase operon (tna) acts strongly. Thus, the desired structural gene is expressed to produce the useful substance in a high yield.

The concentration of glucose in the medium is maintained during the cultivation period of 0.01 to 0.3% (wt/vol), preferably 0.2 to 0.25% (wt/vol), more preferably 0.03 to 0.2% (wt/vol). This enables the use of other industrially expensive carbon sources to be omitted. If desired, other carbon sources such as glycerol, succinic acid, acetic acid, fumaric acid and malic acid may be used together.

Furthermore, L- or DL-tryptophan is also added to the culture medium used in this invention. This enables the gene expression mechanism of the promoter in the tryptophanase operon (tna) to act strongly.

The concentration of L- or DL-tryptophan in the culture medium is not strictly limited. Preferably it is 0.1 to 2 % (wt/vol), more preferably 0.05 to 0.5% (wt/vol). The time of addition of L- or DL-tryptophan may be in an early stage or in an intermediate stage of cultivation, preferably before, the cultivation reaches the later stage of logarithmic growth.

Further, nutrients such as nitrogen sources, inorganic salts and growth promoting substances are properly added to the culture medium used in this invention depending upon the type of the microorganism. Nitrogen sources to be included in the culture medium are, for example, ammonium salts such as ammonium sulfate, ammonium chloride, ammonium nitrate and ammonium phosphate, nitric acid salts such as potassium nitrate, sodium nitrate and ammonium nitrate; organic nitrogen such as glutamic acid, glutamine, aspartic acid and asparagine; and ammonia, to be used either alone or in combination. Examples of the inorganic salts are potassium monohydrogen phosphate, potassium dihydrogen phosphate, magnesium sulfate, iron sulfate and manganese sulfate either alone or in combination. There is no particular restriction on the growth promoter substances, and examples that can be cited are vitamins such as thiamin and biotin, amino acids such as methionine and cystein, and substances wholly or partly containing vitamins or amino acids, such as yeast extract, polypeptone, meat extract, corn steep liquor and Casamino acid.

There is no limitation on the contents of these nutrients in the culture medium, and may be those contents which are used in ordinary cultivations. The nutrients derived from natural materials are suitably contained in amounts of usually 1 to 0.1%, preferably 0.5 to 0.2%, in the culture medium.

The cultivation of the microorganism in the culture medium having the above composition may be carried out under aerobic conditions by using the same cultivation device as used normally. By passing air or another oxygen-containing gas, through the culture medium and/or stirring the culture medium, the concentration of the dissolved oxygen in the culture medium may be maintained generally at 1 to 8 ppm, preferably at 2 to 7 ppm, and the cultivation can be performed more effectively.

The addition of glucose to the culture broth may be carried out continuously, or intermittently at a certain time interval or while monitoring the concentration of glucose.

The "concentration of glucose" may be measured, for example, by using the glucose A Test Wako (a product of Wako Pure Chemicals, Co., Ltd.) or a glucose analyzer GLU-1 (a product of Toa Denpa Co., Ltd.), and the "concentration of dissolved oxygen" may be measured by a DO converter (a product of Oriental Electric Co., Ltd.).

The cultivation conditions may be selected so as to be suitable for the type of the transformed microorganism. Generally, the cultivation temperature is about 10° to about 45° C., preferably about 25° to about 40° C., and the pH of the culture medium may be maintained at about 3 to 10, preferably about 5 to 9. Where the pH of the culture medium varies during the cultivation, alkalies such as ammonia, sodium hydroxide, potassium hydroxide, sodium carbonate and sodium hydrogen carbonate, or acids such as sulfuric acid and hydrochloric acid are desirably added to adjust the pH. The cultivation time may be adjusted usually to about 5 to 48 hours.

By performing the cultivation as described above the useful product encoded by the structural gene can be accumulated in very large amounts in the microbial cells or the culture broth. The useful substance can be recovered from the microbial cells or the culture broth by known methods such as centrifugal separation and ultra-filtration.

The following examples illustrate the present invention more specifically. It should be understood that these examples are given as an aid to an understanding of the present invention, and do not limit the scope of the invention in any way.

EXAMPLES

In these examples, (1) the number of recognition sites of restriction endonucleases, and the sizes of the fragments, (2) the tryptophanase activity, (3) the tryptophan synthase activity, (4) chloramphenicol acetyltransferase (CAT) activity, (5) the amounts of proteins and glucose in a sample enzyme solution and (6) the amounts of the cells harvested and (7) dissolved oxygen concentration were measured by the following methods (1) Number of recognition sites by restriction endonuclease and the size of a fragment:

The "number of recognition sites" by a restriction endonuclease can be determined from the number of separable fragments which is examined by completely digesting the DNA fragment or plasmid with an excess of a restriction endonuclease and subjecting the digestion product to agarose gel electrophoresis and polyacrylamide gel electrophoresis.

The "size of a fragment" and the sizes of the individual DNA fragments of a plasmid are calculated on the basis of a standard line drawn by migration distances on the same agarose gel of a DNA fragment of a (lambda) known molecular size obtained by digesting DNA of φ (phi) phage of *Escherichia coli* with restriction endonuclease HindIII when agarose gel electrophoresis is used; and on the basis of a standard line drawn by migration distances on the same polyacrylamide gel of a DNA fragment of a known molecular size obtained by digesting DNA of φ (phi) phage of *Escherichia coli* with restriction endonuclease HaeIII. The size of the plasmid is calculated by adding the sizes of the individual DNA fragments, fragments of larger than 1 kb is determined by using 1% agarose gel electrophoresis, and fragments of about 0.1 kb to less than 1 kb, by using a 4% polyacrylamide gel electrophoresis.

(2) Tryptophanase activity

Cells harvested by centrifugation (4000 rpm, 15 minutes, 4° C.) from 20 ml of the culture broth, were suspended in 20 ml of a 100 mM phosphase buffer (pH 8.0) again centrifuged (4000 rpm 15 minutes, 4° C.). The cells harvested were suspended in 2 ml of the same buffer as above, and disrupted by ultrasonication (Sonifier 200 made by Branson). The sonicate was centrifuged (12000 rpm, 40 minutes, 4° C.), and the supernatant was used as a sample enzyme solution.

The above enzyme solution was diluted with a proper amount of 100 mM phosphate buffer (pH 8.0) and 0.1 ml of the diluted solution was added to a test tube containing 0.9 ml of a reaction solution [a 100 mM phosphate buffer (pH 8.0) containing 10 mM of L-tryptophan and 0.04 mM of pyridoxalphosphate]. At 37° C. the mixture was subjected to reaction under shaking in a constant temperature water vessel for 20 minutes. The reaction was stopped by adding 1 ml of 10% (wt/vol) trichloroacetic acid the mixture was again centrifuged as above (4000 rpm, 15 minutes, 4° C.) and indole in the supernatant was quantitatively determined by gas chromatography CC-3BF, made by Shimazu Seisakusho). The tryptophanase activity was calculated as the amount of indole formed per hour per unit amount of protein, and was expressed as a relative value by taking the activity in a comparative example as 1.

(3) Tryptophan synthase activity

Cells harvested by centrifugation (4000 rpm, 15 minutes, 4° C.) from 20 ml of the culture broth was suspended in 20 ml of 100 mM Tris-HCl buffer (pH 7.8), and again centrifuged (4000 rpm, 15 minutes, 4° C.). The cells were harvested and suspended in 2 ml of the above buffer and disrupted by ultrasonication (Sonifier 200, made by Branson). The sonicate was centrifuged (12000 rpm, 40 minutes, 4° C.). The resulting supernatant was used as a sample enzyme solution.

The enzyme activity of the sample solution was carried out in accordance with the method of Yanofsky et al. [Methods in Enzymology, vol. 5, 794 (1962)].

The tryptophan synthase activity was calculated as the amount of indole which formed per hour per unit amount of protein, and was expressed as a relative value when the activity in a comparative example was taken as 1.

(4) Activity of chloramphenicol acetyl transferase (CAT) activity

The culture broth was centrifuged, and the cells were harvested. The cells were washed with 50 ml of 10 mM Tris buffer (pH 7.8). The washed cells were again centrifuged, and the cells were harvested to obtain 200 mg of wet cells. The harvested cells were suspended in 1 ml of a 10 mM Tris buffer (pH 7.8), and ultrasonicated. The enzyme activity was measured by the method of W. V. Shaw et al. [Methods in Enzymology, Academic Press, New York (1975), vol 43, p. 737] after the resulting cell debris was properly diluted with a 10 mM Tris buffer. Chloramphenicol acetyltransferase activity was calculated as the amount of chloramphenicol acetylated per minute per unit amount of protein, and expressed as a relative value when the activity in a comparative example was taken as 1.

(5) The amount of protein in the sample enzyme solution was measured by the method of Lowry et al. (Journal of Biological Chemistry, vol 193, p. 265, 1951), and the amount of glucose in the enzyme solution, by the glucose C test Wako (made by Wako Pure Chemicals Co., Ltd.).

(6) Amount of cells harvested

The amount of wet cells harvested were measured after centrifuging (8000 rpm, 20 minutes 4° C.) 50 ml of the culture broth.

(7) Dissolved oxygen concentration

The dissolved oxygen concentration was measured by a DO converter (made by Oriental Electric Co., Ltd.)

EXAMPLE 1

Preparation of plasmid pMTP4 and transformation of Escherichia coli K-12 strain with plasmid pMTP4

(1) Preparation of a DNA fragment containing a promoter in the tryptophanase operon (tna), a regulatory gene tnaC located downstream of the promoter and a tryptophanase structural gene (tnaA):

100 ml of an L-broth (10 g of trypton, 5 g of yeast extract, 1 g of glucose, 5 g of NaCl, 1 liter of distilled water; pH 7.2) was put in a 500 ml Erlenmeyer flask, and sterilized at 120° C. for 15 minutes.

*Escherichia coli* K-12 (ATCC 27325) was inoculated in this culture medium, and cultivated at 37° C. for 15 hours. Then, 2 ml of of the culture broth was taken, and then inoculated to in 100 ml of the culture medium and again cultivated at 37° C. for 4 hours.

After the broth the entire cultivation was centrifuged (8000X g, 15 minutes, 4° C.), and the cells were harvested. The cells were then suspended in 50 ml of a solution containing 50 mM Tris buffer (pH 8.0) and 10 mM EDTA.2NA. Then, lysozyme was added so that its final concentration reached 2 mg/ml. After standing for 5 minutes, 6 ml of a 10% solution of sodium dodecyl sulfate was added, and the mixture was incubated at 65° C. for 30 minutes. To this lyzate, 15 ml of a 5M NaCl was added, and the mixture was cooled at 0° C. for 1 hour. The entire mixture was centrifuged (12000 x g, 60 minutes, 4° C.), to collect the supernatant fraction, twice volume of ethanol was added and mixed. After mixing, the mixture was centrifuged (5000 x g, 10 minutes, 4° C.). The resulting precipitate was dissolved in 10 mM Tris buffer (pH 7.5)-1 mM EDTA.2NA solution, and the solution was extracted with phenol (to remove protein) and treated with ribonuclease to give 1.5 mg of DNA.

The so prepared chromosomal DNA (25 micrograms) was digested with 5 units each of restriction endonucleases HindIII and BamHI at 30° C. for 1 hour. pBR322 (1 microgram) was digested with 1 unit each of restriction endonucleases HindIII and BamHI at 30° C. for 1 hour. The resulting digestion product solution was mixed with the above chromosomal digest. The mixture was made to 50 mM Tris buffer (pH 7.6), 10 mM dithiothreitol, 1 mM ATP, 10 mM MgCl$_2$ and 1 unit of T4 ligase (all of which are the final concentrations) and ligation was done at 16° C. for 15 hours. By using the resulting solution, *Escherichia coli* K-12 strain (tryptophanase-deficient tryptophan auxotraph) was transformed by a conventional method [M. Mandel and A. Higa: J. Mol. Biol., 53, 159 (1970)], and then spread over a selective medium consisting of 7 g of K$_2$HPO$_4$ 2 g of KH$_2$PO$_4$, 1 g of (NH$_4$)$_2$SO$_4$, 0.1 g of MgSO$_4$.7H$_2$O, 5 g of Casamino acids, 10 mg of indole, 50 mg of adenine, 2 g of succinic acid, 20 g of agar, and 1 liter of deionized water. The cells which grew on the selective medium were inoculated to an L-broth to which ampicillin was added in a final concentration of 50 micrograms/ml, and cultivated at 37° C. for 7 hours. The cells were harvested by centrifugation (8000X g, 10 minutes, 4° C.), and the tryptophanase activity was examined.

50 mg of wet cells were added to 1 ml of a reaction solution for measurement of the tryoptophanase activity (0.1M phosphate buffer pH 8.0, 10 mM tryptophan, 0.1% Triton X-100), and reacted at 37° C. for 30 minutes. Indole formed was reacted with p-dimethylbenzaldehyde and spectrophotometically quantitated. Some strains exhibit high activity and from these cells a plasmid was extracted by the alkaline SDS method. [T. Maniatis, E. F. Fritsch and J. Sambrook: "Molecular Cloning" (1982) pages 90 to 91] and digested with BamHI and HindIII. Fragment length of the digest was determined by using an agarose gel. It was found that a DNA fragment of about 3.2 kb was inserted into the HindIII and BamHI sites of pBR322 (this plasmid will be referred to as pBR322tna).

The resulting transformants were cultivated in a liquid medium, and plasmid pBR322tna was purified. The plasmid DNA was completely digested with restriction endonucleases BamHI and HindIII at 37° C. for 1 hour. The digestion product was separated by 0.8% agarose gel electrophoresis, and from the gel, a DNA fragment (about 3.2 kb) containing tryptophanase structural gene was cut out. DNA was extracted, and purified. This DNA fragment was then introduced into plasmid pUC119, and pUC119tna was prepared as follows.

The plasmid pUC119 is a plasmid of about 3.1 kb which can replicate in *Escherichia coli* and expresses ampicilin resistance. It can be purchased from Takara Shuzo Co., Ltd., Japan.

The plasmid pUC119 (0.9 micrograms) was completely digested with restriction endonucleases BamHI and HindIII at 37° C. for 1 hour. The digestion product was mixed with a BamHI and HindIII DNA fragment containing the tryprophanase structural gene (tnaA). To inactive the restriction endonucleases, the mixture was heat-treated at 65° C. for 10 minutes. As final concentrations, 50 mM Tris buffer (pH 7.6), 10 mM MgCl$_2$, 10 mM dithiothreitol, 1 mM ATP and 1 unit of T4 DNA ligase were added to the heat-treated solution, and the solution were maintained at 16° C. for 15 hours. *Escherichia coli* JM109 competent cells (a product of Takara Shuzo Co., Ltd.) were transformed by using the resulting solution.

The transformants were cultivated for 24 hours in L-broth (10 g of Trypton, 5 g of yeast extract, 5 g of NaCl, 20 g agar, 1 liter of deionized water, pH 7.2) containing 50 micrograms/ml (final concentration) of ampicillin, 100 micrograms/ml (final concentration) of IPTG (isopropylbeta-D-thiogalactopyranoside), and 100 micrograms/ml (final concentration, of X-gal (5-bromo-4-chloro-3-indolyl-beta-D-galactopyranoside). Among the colonies formed on the plate, those which grew in white colonies were selected, and the plasmids were extracted by the alkaline SDS method [T. Maniatis, E. F. Fritsch and J. Sambrook, "Molecular Cloning" (1982) pages 90 to 91] (the resulting plasmid will be referred to as pUC119tna).

The plasmid pUC119tna DNA was completely digested with restriction endonucleases BamHI and BbeI at 37° C. for 1 hour. From this 3.2 kb fragment, an about 900 bp region from the BamHI site was deleted with exonuclease II (a product of Takara Shuzo Co., Ltd.), and the Bbe I site was made a blunt end by treatment with S1 nuclease (a product of Takara Shuzo, Co., Ltd.). Then, the fragment was mixed with a Bam HI linker (a product of Takara Shuzo Co., Ltd.), and 50 mM Tris buffer (pH 7.6), 10 mM of MgCl$_2$ and 1 unit of T4 DNA ligase were added (these concentrations were final concentrations), and incubated at 16° C. for 15 hours to perform ligation and reconstruct the plasmid.

*Escherichia coli* K-12 strain (tryptophanase-deficient and tryptophan-requiring strain) was transformed using the resulting plasmid solution in a customary manner [M. Mandel, A. Higa: J. Mol. Biol., 53 159 (1970)], and coated on spread over a selective medium [7 g of K$_2$HPO$_4$, 2 g of KH$_2$PO$_4$, 1 g of (NH$_4$)$_2$SO$_4$, 0.1 g of MgSO$_4$.7$_2$O, 5 g of Casamino acids, 10 mg of indole, 50 mg of adenine, 2 g of glucose, 20 g of agar, and 1 liter of deionized water].

The transformants were then cultured in a liquid broth, and the plasmid DNA was extracted from the culture broth. The plasmid DNA was completely digested with restriction endonucleases BamHI and HindIII at 37° C. for 1 hour, and separated by 0.8% agarose gel electrophoresis to select a transformant which showed two bands (about 2.9 kb pUC119 portion and about 2.3 kb tna portion) on the gel. This DNA fragment of about 2.3 kb containing the tryprophanase promoter, the regulatory gene tnaC and the tryprophanase structural gene (tnaA) was extracted and purified from the cut-out gel piece.

Then, the plasmid pBR322 DNA was completely digested with restriction endonucleases BamHI and HindIII at 37° C. for 1 hour, and the digestion product was mixed with the about 2.3 kb fragment. The mixture was heat-treated at 65° C. for 10 minutes to inactive the restriction endonucleases. Then, 50 mM Tris buffer (pH 7.6), 10 mM dithiothreitol, 1 mM ATP, 10 mM MgCl$_2$ and 1 unit of T4 DNA ligase were added (the concentrations were final concentrations), and reacted at 16° C. for 15 hours to perform ligation. *Escherichia coli* HB101 competent cells (a product of Takara Shuzo Co., Ltd.) were transformed by the resulting solution. The resulting transformants were cultivated in a culture medium, and the plasmid DNA was extracted from the culture broth. The plasmid DNA was analyzed by using restriction endonucleases BamHI and HindIII. A 2.3 kb DNA was seen to be inserted into the BamHI and HindIII sites of pBR322 (this plasmid will be referred to as pBR322tnal).

(2) Preparation of a mini-F fragment

*Escherichia coli* K-12 strain (ATCC 15153) was inoculated in one liter of L-broth (Trypton 10 g, yeast extract 5 g, NaCl 5 g, glucose 1 g, water 1 liter; pH 7.2), and cultivated with shaking at about 37° C. for 4 hours. The cells were harvested, treated with lysozyme, and lyzed with sodium dodecylsulfate (SDS). The lysate was centrifuged for 40 minutes at 32,000 x g. The supernatant was separated, subjected to cesium chloride-ethidium bromide equilibrium density gradient centrifugation and then dialyzed to separate a solution containing the F plasmid. Plasmid DNA was precipitated with ethanol and finally about 20 micrograms of F plasmid DNA was collected.

Then, 5 micrograms of the F plasmid was taken and subjected to digestion with restriction endonuclease EcoRI for 1 hour at 37° C. to cleave the DNA. As a result, a DNA solution containing a mini-F fragment having a size of about 9.2 kb was prepared.

(3) Preparation of the desired plasmid

The plasmid pBR322tnaI DNA obtained in section (1) above was completely digested with restriction endonuclease EcoRI at 37° C. for 1 hour. The digestion product was mixed with the mini-F fragment obtained in section (2). The mixture was heat-treated for 10 minutes at 65° C. to inactive the restriction endonuclease. Then, 50 mM Tris buffer pH 7.6, 10 mM $MgCl_2$, 1 mM ATP and 1 unit of T4 DNA ligase were added (the concentrations were final concentrations), and the mixture was kept cool at 16° C. for 15 hours to perform ligation (this plasmid will be provisionally called pBR322Ftna).

(4) Transformation of Escherichia coli K-12 strain by plasmid pMTP4

Using the plasmid DNA prepared in section (3), Escherichia coli K-12 strain (ATCC 27325) was transformed in a customary manner to obtain transformants. They were cultivated in a liquid culture medium, and the plasmid pBR322Ftna was separated and purified, and named plasmid pMTP4.

This plasmid pMTP4 was digested with various restriction endonucleases, and the molecular sizes of the fragments were measured. The results are shown in Table 1.

TABLE 1

| Restriction endonuclease | Number of recognition sites | Molecular size (megadaltons; kb in the parentheses) |
|---|---|---|
| EcoRI | 2 | 6.1 (9.2), 4.2 (6.3) |
| BamHI | 3 | 1.6 (2.4), 7.1 (10.7) |
|  |  | 1.6 (2.4) |
| HindIII | 2 | 9.8 (14.7), 0.5 (0.8) |

The restriction endonuclease cleavage map of the plasmid pMTP4 is shown in FIG. 1.

Escherichia coli YK3007 transformed with the plasmid pMTP4 was deposited on Feb. 16, 1989 at Fermentation Research Institute, Agency of Industrial Science and Technology, Japan, 1-1-3, Higashi, Tsukubashi, Ibaraki-ken, Japan under FERM P-10543 (transferred to international deposition FERM BP-2803 on Mar. 14, 1990 under the Budapest Treaty).

(5) Stability of transformed E. coli YK3007

100 ml of the above L-broth containing 2 g/liter of glucose as a carbon source was put in a 500 ml Erlenmeyer flask, and sterilized at 120° C. for 15 minutes. The transformants obtained in Example 1 were inoculated, and cultivated under shaking at 37° C. for 24 hours. The culture was inoculated to the same medium prepared and sterilized as above at the concentration of 50 cells per ml medium and was cultivated at 37° C. for 24 hours under shaking.

Then the cells were harvested by centrifugation, and washed. They were appropriately diluted and spread over L-broth agar plate (2% agar) with or without ampicillin (50 μg/ml), and cultivated for one day at 37° C. The grown colonies were counted.

As a result, it was found that the number of colonies grown on the ampicillin-containing L-broth was the same as those grown on the L-broth to which no additional component was added. It was also confirmed that the colonies grown on the L-broth all grew on a minimum medium (containing 10 mg/l of indole) containing no tryptophan. In other words, the stability of the plasmid was very high.

EXAMPLE 2

Preparation of plasmid pMTY20 and transformation of Escherichia coli K-12 strain with the plasmid pMTY20

(1) Preparation of a DNA fragment containing tryptophan synthase structural genes (trp A, trp B)

(A) Preparation of phage φ (phi) 80 pt

Escherichia coli K-12 strain (ATCC 27325) was inoculated in 100 ml of L-broth (having the same composition as indicated above), and cultivated with shaking at 37° C. for 4 hours. 0.5 mg of the culture broth was mixed with 0.1 ml of an aqueous solution of phage φ (phi) 80 (ATCC 11456a-B1) ($10^5$/ml) in L-broth soft agar (L-broth + agar powder), and the mixture was overlaid on an L-broth agar plate. When the plate was cultivated at 37° C. for about 5 hours, plaques formed. When the cultivation was continued further for 2 to 3 days at 37° C., grown colonies of phage φ (phi) 80 lysogenic bacteria formed in the plaque. The lysogenic bacteria were cultivated in L-broth at 37° C. for 4 hours and plated on the same L-broth agar plate, phage φ (phi) 80 pt (a phage DNA containing tryptophan operon) was prepared by induction with ultraviolet radiation (400–800 ergs/$mm^2$, 10–20 seconds).

(B) Preparation of a tryptophan operon DNA fragment Escherichia coli K-12 strain (ATCC 27325) was inoculated in 1 liter of L-broth having the same composition as indicated above, and cultivated with shaking at about 37° C. for about 3 hours. In the logarithmic growth phase 10 ml of a 25% (w/v) glucose solution and the phage φ (phi) 80 pt solution prepared in (A) were added (moi 20) in a concentration of $10^{11}$/ml. The shaking culture was continued for 5 hours, and by the addition of chloroform, a large amount of phage φ (phi) 80 pt was prepared [see T. Maniatis, E. F. Fritsch, and J. Sambrook: "Molecular Cloning" (1982), pages 76–80, Cold Spring Harbor Laboratory].

The phage φ (phi) 80 pt solution obtained was dialyzed against Tris buffer (pH 7.8), and by the DNA extracting method using phenol (see page 85 of the above-cited "Molecular Cloning"), the phage DNA was recovered and purified. The phage DNA was digested with restriction endonuclease BamHI at 30° C. for 30 minutes to obtain a tryptophan operon DNA fragment (size: about 20 kb).

(C) Preparation of plasmid pBR322trp

The tryptophan operon fragment obtained in (B) was digested with restriction endonucleases SalI and XhoI at 37° C. for 1 hour to cut out a DNA fragment having a molecular size of about 7.4 kb. Then, the solution was heat-treated at 65° C. for 5 minutes to inactivate the restriction endonucleases. It was then mixed with plasmid pBR322 treated with restriction endonuclease SalI. Then, 50 mM Tris buffer (pH 7.6), 10 mM $MgCl_2$, 10 mM dithiothreitol, 1 mM ATP and 1 unit of T4 DNA ligase (the concentrations were final concentrations).

The mixture was kept cool at 16° C. for 15 hours to perform ligation of DNA.

By using the circularized DNA, *Escherichia coli* K-12 strain (tryptophan-requiring; ATCC 23718) was transformed to obtain transformants [disappearance of tryptophan-requirement]. By trpA, trpB genes on the plasmid, biosynthesis of tryptophan became possible and the transformants could grow on a minimum medium (7 g of $K_2HPO_4$, 2 g of $KH_2PO_4$, 0.1 g of $MgSO_4.7H_2O$, 1 g of $(NH_4)_2SO_4$, 1 liter of deionized water). These transformants were cultivated in a liquid culture medium, and from the culture broth, a plasmid was separated and purified (this plasmid will be referred to as pBR322trp).

(D) Cloning of tryptophan synthase structural genes (trpA, trpB):

The plasmid pBR322 trp obtained in section (C) was digested at 37° C. for 1 hour with restriction endonucleases SacII and SalI to obtain a fragment having a molecular size of about 3.5 kb and containing trp A, trp B genes. Then, it was partially digested with restriction endonuclease HincII at 37° C. to obtain a minimum fragment having a molecular size of about 2.6 kb and containing trp A and trp B. This fragment was mixed with a SalI linker, and ligated by a T4 DNA ligase to give a fragment containing trp A and trp B and having a SalI site at both ends.

(2) Preparation of a DNA fragment containing a tryptophanase promoter and regulatory gene tnaC located downstream of the promoter (A) Preparation of choromosomal DNA of *E. coli* K-12 strain (ATCC27325)

100 ml of L-broth (10 g of Trypton, 5 g of yeast extract, 1 g of glucose, 5 g of NaCl, 1 liter of deionized water; pH 7.2) was put in a 500 ml Erlenmeyer flask, and sterilized at 120° C. for 15 minutes. *E. coli* K-12 strain (ATCC 27325) was inoculated in this medium, and cultivated at 37° C. for 15 hours. This culture broth (2 ml) was taken, and inoculated newly in 1000 ml of the above medium, and again cultivated at 37° C. for 4 hours.

After the cultivation, all the culture broth was centrifuged (8,000 rpm, 15 minutes, 4° C.) to harvest the cells. Then, the cells were suspended in 50 ml of 10 mM EDTA.2NA solution 50 mM Tris buffer (pH 8.0). Then, lysozyme was added to the final concentration reached 2 mg/ml. After standing for 5 minutes, 6 ml of a 10% solution of sodium dodecylsulfate was added, and the mixture was heated at 65° C. for 30 minutes and lyzed. To this lysis solution was added 15 ml of 5M NaCl solution, and the mixture was cooled at 0° C. for 1 hour. All the mixture was centrifuged (12,000 rpm, 60 minutes, 4° C.). The supernatant fraction was taken, and 6 times its weight of ethanol was added. The mixture was centrifuged (5,000 rpm, 10 minutes, 4° C.). The precipitate was dissolved in 10 mM Tris buffer (pH 7.5)-1 mM EDTA.2NA solution, and treated with phenol (protein-eliminating treatment) and with an ribonuclease to finally give 1.5 mg of DNA.

(B) Preparation of a DNA fragment containing a tryptophanase promoter and a regulatory gene tnaC located downstream of the promoter:

The chromosomal DNA prepared in (A) above (25 micrograms) was digested at 30° C. for 1 hour with restriction endonucleases HindIII and BamHI (each 5 units). With this digest was mixed 1 microgram of plasmid pBR322, digested with 1 unit each of restriction endonucleases HINDIII and BamHI at 39° C. for 1 hour. 50 mM Tris buffer (pH 7.6), 10 mM dithiothreitol, 1 mM ATP, 10 mM $MgCl_2$ and 1 unit of T4 DNA ligase (the concentration were final concentrations) were added to the mixture and incubated at 16° C. for 15 hours.

*E. coli* K-12 strain (tryptophanase-deficient and tryptophan requiring mutant) was with the ligated as above in a customary manner [M. Mandel, A. Higa: J. Mol. Biol., 53, 159 (1970), and spread over on a selective medium [7 g of $K_2HPO_4$, 2 g of $KH_2PO_2$, 1 g of $(NH_4)_2SO_4$, 0.1 g of $MgSO_4.7H_2O$, 5 g of Casamino acids, 10 mg of indole, 2 g of adenine, 20 g of agar, 50 mg of succinic acid and 1 liter of deionized water]. The colonies formed on the agar plate were inoculated to L-broth supplemented with ampicillin (50 micrograms/ml as a final concentration), and cultivated at 37° C. for 7 hours. The cells were harvested by centrifugation (8,000 rpm, 10 minutes, 4° C., and their tryptophanase activity was examined. To 1 ml of a reaction solution (0.1M phosphate buffer pH 8.0; 10 mM tryptophan, 0.1% Triton X-100) were added 50 mg of wet cells, and reacted at 37° C. for 30 minutes. The resulting indole was reacted with p-dimethylbenzaldehyde and some strains exhibited tryptophan degrading activity. The plasmid was extracted from these cells by using the alkaline-SDS method [T. Maniatis, E. F. Fritsch, and J. Sambrook: "Molecular Cloning" (1982), see pages 90 to 91]. The plasmid was cleaved with restriction endonucleases BamHI and HindIII, and the molecular size was examined by using agarose gel. A DNA having a molecular size of about 3.2 kb was seen to be inserted into the HindIII and BamHI sites of the plasmid pBR322 (this plasmid will be referred to as pBR322tna).

The resulting pBR322tna was digested with restriction endonucleases AluI and RsaI at 37° C. for 1 hour to give a fragment having a molecular size of about 630 bp containing the tryptophanase promoter and the regulatory gene tnaC. This fragment was mixed with a BamHI linker and ligated with T4 DNA ligase to attach BamHI sites on both ends.

(3) The DNA fragment obtained in section (1) above and the DNA fragment in section (2) above were inserted by a conventional method into the SalI site and BamHI site of plasmid pUC119 (a product of Takara Shuzo Co., Ltd.) Then, this plasmid was digested partially with restriction endonucleases EcoRI and HindIII to cut out a DNA fragment containing the tryptophanase promoter, the regulatory gene tnaC, and the tryptophan synthase structural gene (trp B, trp A). This DNA fragment was inserted in a customary manner into the EcoRI and HindIII sites of the plasmid pBR322. Furthermore, the mini-F fragment prepared in Example 1, (2) was inserted in a customary manner into the EcoRI site of this plasmid to prepare the desired plasmid.

(4) Transformation of *E. coli* K-12 strain with plasmid pMTY20.

A tryptophanase-deficient strain was isolated from *E. coli* K-12 strain (ATCC 27325) by a conventional method ("Molecular Biology Experimental Manual" edited by Masaya Kawakami, page 20, 1984, published by Kodansha, Tokyo). This cell was used as a host and transformed with the plasmid DNA prepared in section (3) above. The transformants were cultivated in a customary manner in a liquid medium, and the plasmid was separated and purified. The resulting plasmid was named pMTY20.

Figure 2:
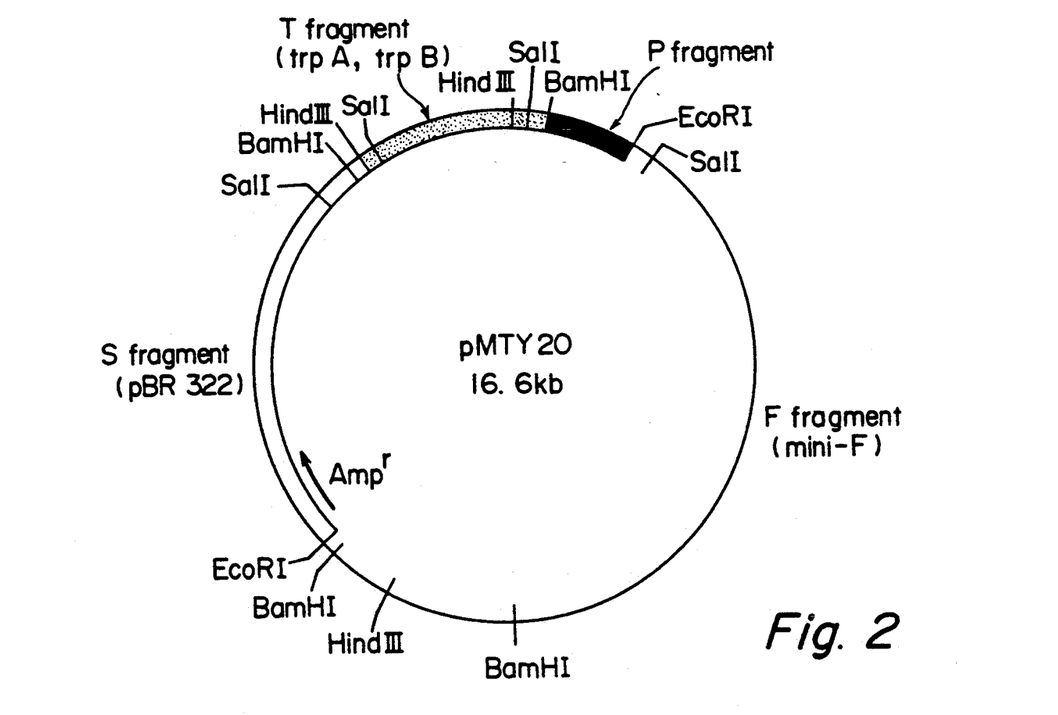
FIG. 2 shows plasmid pMTY20 which comprises
(a) a DNA fragment (P fragment) containing a tryptophanase promoter and a regulatory gene tnaC located downstream of the promoter,
(b) a DNA fragment (T fragment) containing tryptophan synthase structural genes (trpA, trpB),
(c) a DNA fragment (S fragment) containing the replication origin of plasmid pBR322, and
(d) a mini-F fragment (F fragment) obtained from F-plasmid.

The plasmid pMTY20 was digested with various restriction endonucleases, and the molecular sizes of the fragments were measured. The results are shown in Table 2.

TABLE 2

| Restriction endonuclease | Number of recognition sites | Molecular size (megadaltons; kb in the parentheses) |
|---|---|---|
| EcoRI | 2 | 5.5 (9.2), 4.4 (7.4) |
| HindIII | 3 | 5.6 (9.3), 3.0 (5.0) 1.3 (2.3) |
| SalI | 4 | 7.7 (12.8), 1.4 (2.4) 0.5 (0.8), 0.3 (0.6) |
| BamHI | 5 | 4.1 (6.8), 2.4 (4.0) 1.6 (2.7), 1.4 (2.4) 0.4 (0.7) |

The restriction endonuclease map of the plasmid pMTY20 is shown in FIG. 2.

*Escherichia coli* YK2017 transformed with the plasmid pMTY20 was deposited on Nov. 17, 1989 at Fermentation Research Institute, Agency of Industrial Science and Technology, Japan, 1-1-3, Higashi, Tsukuba-shi, Ibaraki-ken Japan under FERM P-11117 (transferred to international deposition FERM BP-2804 on Mar. 14, 1990 under the Budapest Treaty).

(5) Stability of the transformed *Escherichia coli* YK2017

100 ml of the above L-broth containing 2 g/liter of succinic acid in place of 1 g/liter of glucose as a carbon source was put in a 500 ml Erlenmeyer flask and sterilized at 120° C. for 15 minutes. The transformed cells *Escherichia coli* YK2017 obtained in section (4) above were inoculated in the L-broth, and cultivated under shaking at 37° C. for 24 hours. The culture was inoculated to the same medium prepared and sterilized as above at the concentration of 50 cells per ml medium and was cultivated at 37° C. for 24 hours under shaking.

Then, the cells were harvested by using centrifugation. The cells were washed, and then appropriately diluted a and spread over L-broth agar plate (agar: 2%) with or without ampicillin (50 mg/ml) and cultivated at 37° C. for 1 day. After the cultivation, the colonies which grew were counted.

It was found that the number of colonies which appeared on the ampicillin-containing medium was the same as that which grew on the medium without ampicillin. Furthermore, all colonies which grew on the L-broth grew on a minimum medium (containing 10 mg/liter of indole) containing no tryptophan. This led to the determination that the plasmid has high stability.

EXAMPLE 3

Preparation of plasmid pCAT-1 and the transformation of *E. coli* K-12 strain with the plasmid pCAT-1

(1) Preparation of plasmid pCAT-1

The about 630 bp DNA fragment having a BamHI site at both ends and containing the tryptophanase promoter and regulatory gene tnaC located downstream of the promoter obtained in Example 2, (2) was inserted by a conventional method into the BamHI site of plasmid pKK232-8 (purchased from Pharmacia Co., Ltd.) bearing a chloramphenicol acetyltransferase structural gene (about 0.66 kb) having no promoter of itself to prepare plasmid pKK232-8CAT. The mini-F DNA fragment (about 9.2 kb) obtained in Example 1, (2) was inserted into the Sma I site of the pKK232-8CAT. This plasmid will be named as pCAT-1.

Figure 3:
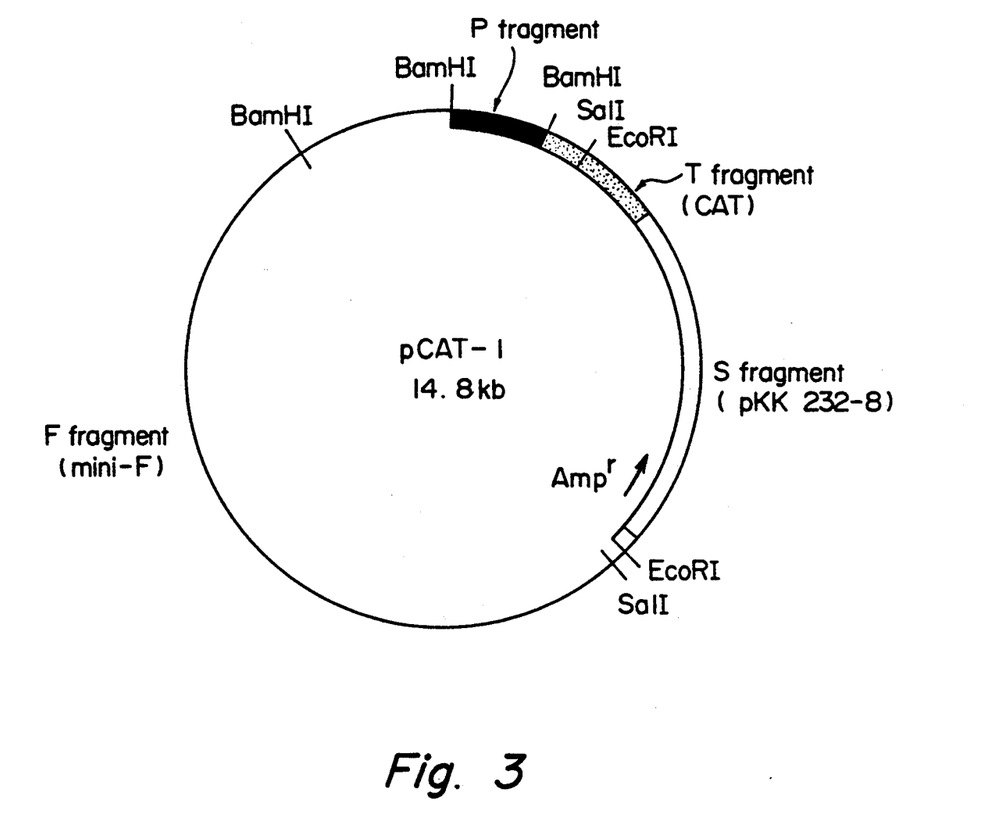
FIG. 3 shows plasmid pCAT-1 which comprises
(a) a DNA fragment (P fragment) containing a tryptophanase promoter and a regulatory gene tnaC located downstream of the promoter, and
(b) a DNA fragment (T fragment) containing a chloramphenicol acetyltransferase structural gene,
(c) a DNA fragment (S fragment) containing the replication origin of plasmid pKK232-81, and
(d) a DNA fragment (F fragment) obtained from F-plasmid.

The plasmid pCAT-1 was cleaved with various restriction endonucleases. Table 4 shows the molecular sizes of the various cleaved fragments. The restriction cleavage map of the plasmid pCAT-1 is shown in FIG. 3.

TABLE 3

| Restriction endonuclease | Number of recognition sites | Molecular size (megadaltons; kb in the parentheses) |
|---|---|---|
| EcoRI | 2 | 6.6 (10.0), 3.1 (4.7), 0.07 (0.1) |
| BamHI | 3 | 7.67 (11.5), 1.7 (2.6), 0.4 (0.7) |
| SalI | 2 | 6.47 (9.8), 3.3 (5.5) |

(2) Transformation of *E. coli* K-12 strain with plasmid pCAT-1 *Escherichia coli* K-12 strain (ATCC 27325) was used as a host, and transformed in a customary manner by using plasmid pCAT-1 DNA prepared in Section (1) above. The resulting transformant was named *Escherichia coli* CAT-1.

(3) Stability of the transformant *Escherichia coli* CAT-1

100 ml of the above L-broth (containing 2 g/liter of succinic acid instead of 1 g/liter of glucose as a carbon source) was put in a 500 ml Erlenmeyer flask, and sterilized at 120° C. for 15 minutes. The transformants *Escherichia coli* CAT-1 obtained in section (2) were inoculated in the sterilized L-broth and then cultivated with shaking at 37° C. for 24 hours. Then, 100 ml of the same medium as prepared above was put in a 500 ml Erlenmeyer flask, and sterilized and the cultivation liquid was inoculated successively at the concentration of 50 cells per ml, and cultivated with shaking at 37° C. for 24 hours.

The cells were harvested by centrifuging and washed. The cells were appropriately diluted and spread over L-broth agar plate with or without ampicillin (50 μg/ml), and cultivated at 37° C. for 1 day. The grown colonies were counted.

It was found that the number of colonies which grew was the same both for the ampicillin-containing medium and the medium not containing it; all colonies which can grow on an L-broth containing chloramphenicol at the concentration of 50 micrograms/ml; namely, this plasmid had high stability.

EXAMPLE 4

Production of tryptophanase by cultivating the transformant *Escherichia coli* YK3007

100 ml of the culture medium shown in Table 4 was put in a 500 ml Erlenmeyer flask and sterilized at 120° C. for 15 minutes. To the sterilized medium one milliliter of a 50% (wt/vol) glucose solution (sterilized at 120° C. for 15 minutes) was aseptically added. Then, *Escherichia coli* YK3007 (FERM BP-2803), a tryptophanase-producing strain, was inoculated, and cultivated with shaking at 37° C. for 1 day. Twenty milliliters of the culture broth was inoculated in 1000 ml of a culture medium prepared so that the concentration of glucose reached the upper limit (wt/vol %) in each run shown in Table 5, and cultivated at 37° C. for 8 hours using an aeration stirred culture tank (600 rpm, aeration 1 vvm, pH 7.2 adjusted with 28% aqueous ammonia). The glucose was used as an 50% (wt/vol) aqueous solution (sterilized at 120° C. for 15 minutes), and added aseptically continuously while periodically, the concentration of glucose in the culture liquid was measured so that the glucose concentration did not exceed the upper limit of the concentration in each run shown in Table 5 and did not fall below 0.01% (wt/vol). The addition was stopped when the total amount of glucose added in each run reached 20 g.

TABLE 4

| | |
|---|---|
| L-tryptophan | 0.5 g |
| KH$_2$PO$_4$ | 1.6 g |
| K$_2$HPO$_4$ | 5.5 g |
| (NH$_4$)$_2$SO$_4$ | 3.0 g |
| MgSO$_4$.7H$_2$O | 0.1 g |
| FeSO$_4$.7H$_2$SO | 80 mg |
| Casamino At (a product of Difco) | 5.0 g |
| Distilled water | 1000 ml |
| (adjusted to a pH of 7.2 with 28% aqueous ammonia) | |

After the end of cultivation, 20 ml fo the culture broth was centrifuged, and the activity of tryptophanase was measured by the method described above. The results are shown in Table 5. As a comparison, the cells cultivated by adding 20 g/liter of glucose at the start of the cultivation were used.

TABLE 5

| Upper limit of the glucose concentration in the culture broth (wt/vol %) | Relative activity of tryptophanase (*) | Amount of the cells recovered (relative value*) |
|---|---|---|
| 0.1 | 350 | 0.9 |
| 0.2 | 348 | 1.0 |
| 0.3 | 150 | 1.1 |
| 0.4 | 1.1 | 1.1 |
| Comparison (glucose was added at the start of cultivation | 1 | 1 |

(*) Relative value when the activity in the comparison (in which glucose was added in a concentration of 20 g/liter at the start of the cultivation) was taken as 1.

EXAMPLE 5

Production of tryptophan synthase by the cultivation of the transformant E. coli YK2017

One hundred milliliters of the culture medium shown in Table 4 in Example 4 was put in a 500 ml Erlenmeyer flask, and then sterilized at 120° C. for 15 minutes. One milliliter of a 50% (wt/vol) glucose solution (steriliazed at 120° C. for 15 minutes) was aseptically added to the medium in the flask. Then, Escherichia coli YK2017 (FERM BP-2804), (tryptophan synthase-producing strain, was inoculated in the medium, and cultivated at 37° C. for 1 day. The culture broth (20 ml) was inoculated in 1000 ml of a culture medium prepared so that the concentration of glucose became the upper limit of the concentration (wt/vol %) in each run as shown in Table 6, and cultivated at 37° C. for 8 hours by using an aeration stirred cultivation tank (600 rpm, aeration 1 vvm, pH 7.2 adjusted with 28% aqueous ammonia). The glucose was used as an 50% (wt/vol %) aqueous solution (sterilized at 120° C. for 15 minutes), and was added aseptically continuously while periodically, the concentration of glucose in the culture broth was measured so that the glucose concentration did not exceed the upper limit of the concentration in each run shown in Table 6 and did not fall below 0.01% (wt/vol). The addition was stopped when the total amount of glucose added in each run reached 20 g.

At the end of cultivation, 20 ml of the culture broth was centrifuged, and the activity of tryptophan synthase was measured by the method described above.

The results are shown in Table 6. As a comparison, the cells cultivated by adding 20 g/liter of glucose at the start of the cultivation were used.

TABLE 6

| Upper limit of the glucose concentration in the culture broth (wt/vol %) | Relative activity of tryptophan synthase (*) | Amount of the cells recovered (relative value*) |
|---|---|---|
| 0.1 | 220 | 0.9 |
| 0.2 | 211 | 1.0 |
| 0.3 | 85 | 1.1 |
| 0.4 | 1.2 | 1.0 |
| Comparison (glucose was added at the start of cultivation | 1.0 | 1.0 |

(*) Relative value when the activity in the comparison (in which glucose was added in a concentration of 20 g/liter at the start of the cultivation) was taken as 1.

EXAMPLE 6

Production of chloramphenicol acetyltransferase by the cultivation of transformant Escherichia coli CAT-1

One hundred milliliters of the culture medium shown in Table 4 in Example 4 was put in a 500 ml Erlenmeyer flask, and sterilized at 120° C. for 15 minutes. One milliliter of a 50% (wt/vol) glucose solution (sterilized at 120° C. for 15 minutes) was aseptically added. Escherichia coli CAT-1 obtained in Example 3 was inoculated, and then cultivated at 37° C. for 1 day. Then, 20 ml of the culture broth was inoculated in 100 ml of a culture medium prepared so that the concentration of glucose reached the upper limit in each run shown in Table 7, and cultivated by using an aeration stirred culture tank at 37° C. for 8 hours (600 rpm, aeration 1 vvm, pH 7.2 adjusted by adding 28% aqueous ammonia. The glucose was used as an 50% (wt/vol %) aqueous solution (sterilized at 120° C. for 15 minutes), and was added aseptically continuously while periodically, the concentration of glucose in the culture broth was measured so that the glucose concentration did not exceed the upper limit of the concentration in each run shown in Table 7 and did not fall below 0.01% (wt/vol). The addition was stopped when the total amount of glucose added in each run reached 20 g.

After the cultivation, 20 ml of the culture broth in each run was centrifuged, and the activity of chloramphenicol acetyltransferase was measured by the method described above. The results are shown in Table 7. As a comparison, the cells cultivated by adding 20 g/l of glucose at the start of cultivation were used.

TABLE 7

| Upper limit of the glucose concentration in the culture broth (wt/vol %) | Relative activity of chloramphenicol acetyl transferase (*) | Amount of the cells recovered (relative value*) |
|---|---|---|
| 0.1 | 180 | 1.0 |
| 0.2 | 170 | 1.1 |
| 0.3 | 70 | 1.1 |
| 0.4 | 1.3 | 1.0 |
| Comparison (glucose was added at the start of | 1.0 | 1.0 |

TABLE 7-continued

| Upper limit of the glucose concentration in the culture broth (wt/vol %) cultivation | Relative activity of chlorampheni- col acetyl transferase (*) | Amount of the cells recovered (relative value*) |
|---|---|---|

(*) Relative value when the activity in the comparison (in which glucose was added in a concentration of 20 g/liter at the start of the cultivation) was taken as 1.

EXAMPLE 7

Production of tryptophan synthase by the cultivation of transformant *E. coli* YK2017

One hundred milliliter of the culture medium shown in Table 4 in Example 4 was put in a 500 ml Erlenmeyer flask, and sterilized at 120° C. for 15 minutes, and 1 ml of a 50% (wt/Vol) glucose solution (sterilized at 120° C. for 15 minutes) was aseptically added. *Escherichia coli* YK2017 (FERM BP-2804), a tryptophan synthase-producing strain, was inoculated in the resulting medium, and cultivated with shaking at 37° C. for 1 day. Then, 20 ml of the cultured broth was inoculated in 1000 ml of the same culture medium as prepared above, and cultivated at 37° C. in an aeration stirred tank (600 rpm, aeration 1 vvm, pH 7.2 adjusted with 28% aqueous ammonia). The glucose was used as a 50% (wt/vol) aqueous solution (sterilized at 120° C. for 15 minutes). While periodically, the concentration of glucose in the culture broth was measured, glucose was continuously added aseptically so that its concentration did not exceed the upper limit in each run shown in Table 8. When the total amount of glucose in each test area reached 20 g, the addition was terminated.

The concentration of dissolved oxygen in the culture liquid was maintained at the values in each run shown in Table 8 by passing oxygen gas in place of air. In a system through which oxygen was not passed, the concentration of dissolved oxygen became 0 after about 4 hours.

After the cultivation, 20 ml of the cultivation liquid was centrifuged, and the activity of tryptophan synthase was measured by the method described above. As a comparison, the cells obtained by adding 20 g/liter of glucose at the start of the cultivation were used. The results are shown in Table 8.

TABLE 8

| Upper limit of the glucose concentration (wt/vol, %) | Dissolved oxygen concentration of the culture broth (ppm) | Activity of tryptophan synthase (*2) | Amount of cells recovered (* relative value) |
|---|---|---|---|
| 0.1 | No control (*1) | 220 | 1.0 |
|  | 1 | 260 | 1.2 |
|  | 8 | 265 | 1.3 |
| 0.2 | No control | 210 | 1.0 |
|  | 1 | 250 | 1.2 |
|  | 8 | 255 | 1.3 |
| 0.3 | No control | 85 | 1.1 |
|  | 1 | 105 | 1.3 |
|  | 8 | 110 | 1.4 |
| 0.4 | No control | 1.1 | 1.1 |
|  | 1 | 1.3 | 1.3 |
|  | 8 | 1.3 | 1.4 |
| Comparison | No control | 1 | 1.0 |

TABLE 8-continued

| Upper limit of the glucose concentration (wt/vol, %) | Dissolved oxygen concentration of the culture broth (ppm) | Activity of tryptophan synthase (*2) | Amount of cells recovered (* relative value) |
|---|---|---|---|
| (*1) | 1 | 1 | 1.2 |

*1: The cultivation was carried out by adding 20 g/liter of glucose at the start.
*2: relative values when the activity and the amount recovered of cells in the comparison were taken as 1.
*3: the concentration of dissolved oxygen was not controlled by aerating oxygen gas.

We claim:

1. A process for cultivating an *Escherichia coli* K-12 strain transformed with a recombinant plasmid, said plasmid comprising:
    (a) a DNA fragment containing a tryptophanase promoter and a regulatory gene (tnaC) located downstream of said promoter, having a molecular size of about 630 bp prepared by digesting a genomic DNA of *Escherichia coli* with restriction endonucleases BamHI and HindIII to obtain a tryptophanase operon-containing DNA fragment having a molecular size of about 3.2 kb, and further digesting said resultant DNA fragment with restriction endonucleases AluI and RsaI,
    (b) a DNA fragment containing tryptophan synthase structural genes (trpA, trpB), having a molecular size of about 2.6 kb obtained by infecting a genomic DNA of *Escherichia coli* with phage φ (phi) 80 to induce a phase to take up the tryptophan operon in the phase φ (phi) 80 DNA, digesting said phage DNA with a restriction endonuclease BamHI to obtain a DNA fragment having a molecular size of about 20 kb, and further digesting said resultant DNA fragment with restriction endonuclease HincII,
    (c) a DNA fragment obtained from plasmid pBR322 containing at least the genes controlling Col El-type replication, and
    (d) a mini-F fragment having a molecular size of about 9.2 kb prepared by digesting a F-plasmid of *Escherichia coli* with restriction endonuclease EcoRI, said process comprising the steps of:
    cultivating said transformed *Escherichia coli* K-12 strain in a medium containing L- or DL-tryptophan as an inducer of said structural genes and glucose as a carbon source, the concentration of glucose being maintained in a range of 0.01 to 0.3% (wt/vol) by continuous or intermittent addition of glucose to the medium, wherein said structural genes are expressed in said transformed *Escherichia coli* K-12 strain.

2. The process of claim 1 in which the recombinant plasmid is plasmid pMTY20.

3. The process of claim 1 in which the *Escherichia coli* K-12 strain transformed with said recombinant plasmid is *Escherichia coli* YK2017 (FERM BP-2804).

4. The process of claim 1 in which glucose is added to the culture medium continuously or intermittently so that its concentration is maintained at 0.02 to 0.25% (wt/vol).

5. The process of claim 1 in which the concentration of L- or DL-tryptophan in the culture medium is 0.1 to 2% (wt/vol).

6. The process of claim 1 in which the cultivation is carried out under aerobic conditions.

7. The process of claim 1 in which the cultivation is carried out while the concentration of dissolved oxygen in the culture medium is maintained at 1 to 8 ppm.

8. A recombinant plasmid which comprises:
(a) a DNA fragment containing a tryptophanase promoter and a regulatory gene (tnaC) located downstream of said promoter, having a molecular size of about 630 bp prepared by digesting a genomic DNA of *Escherichia coli* with restriction endonucleases BamHI and HindIII to obtain a tryptophanase operon-containing DNA fragment having a molecular size of about 3.2 kb, and further digesting said resultant DNA fragment with restriction endonucleases AluI and RsaI,
(b) a DNA fragment containing tryptophan synthase structural genes (trpA, trpB), having a molecular size of about 2.6 kb obtained by infecting a genomic DNA of *Escherichia coli* with phase φ (phi) 80 to induce a phage to take up the tryptophan operon in the phage φ (phi) 80 DNA, digesting said phage DNA with a restriction endonuclease BamHI to obtain a DNA fragment having a molecular size of about 20 kb, and further digesting said resultant DNA fragment with restriction endonuclease HincII,
(c) a DNA fragment obtained from plasmid pBR322 containing at least the genes controlling Col El-type replication, and
(d) a mini-F fragment having a molecular size of about 9.2 kb prepared by digesting a F-plasmid of *Escherichia coli* with restriction endonuclease EcoRI.

9. The recombinant plasmid of claim 8 which is plasmid pMTY20.

10. *Escherichia coli* YK2017 (FERM BP-2804) containing the plasmid pMTY20.

* * * * *